US012765914B2

(12) United States Patent
Rubbert et al.

(10) Patent No.: US 12,765,914 B2
(45) Date of Patent: Oct. 20, 2026

(54) FLEXIBLE SURGICAL DEVICE WITH CONTROLLABLE STIFFNESS

(71) Applicants: UNIVERSITÉ DE STRASBOURG, Strasbourg (FR); CENTRE NATIONAL DE LA RECHERCHE SCIENTIFIQUE, Paris (FR); INSTITUT NATIONAL DES SCIENCES APPLIQUÉES, Strasbourg (FR); ECOLE POLYTECHNIQUE FEDERALE DE LAUSANNE, Lausanne (CH)

(72) Inventors: Lennart Rubbert, Strasbourg (FR); Charles Baur, Saint-Aubin-Sauges (CH)

(73) Assignees: UNIVERSITÉ DE STRASBOURG, Strasbourg (FR); CENTRE NATIONAL DE LA RECHERCHE SCIENTIFIQUE, Paris (FR); INSTITUT NATIONAL DES SCIENCES APPLIQUÉES, Strasbourg (FR); ECOLE POLYTECHNIQUE FEDERALE DE LAUSANNE, Lausanne (CH)

( * ) Notice: Subject to any disclaimer, the term of this patent is extended or adjusted under 35 U.S.C. 154(b) by 370 days.

(21) Appl. No.: 18/564,774

(22) PCT Filed: May 27, 2022

(86) PCT No.: PCT/EP2022/064460
§ 371 (c)(1),
(2) Date: Nov. 28, 2023

(87) PCT Pub. No.: WO2022/248695
PCT Pub. Date: Dec. 1, 2022

(65) Prior Publication Data

US 2024/0252205 A1 Aug. 1, 2024

(30) Foreign Application Priority Data

May 28, 2021 (EP) .................................... 21305714

(51) Int. Cl.
*A61B 17/34* (2006.01)
*A61B 17/00* (2006.01)

(52) U.S. Cl.
CPC .................... *A61B 17/3417* (2013.01); *A61B 2017/00309* (2013.01)

(58) Field of Classification Search
CPC ...... A61B 17/3417; A61B 2017/00309; A61B 2017/00314; A61M 25/0053; A61M 25/0054
See application file for complete search history.

(56) References Cited

U.S. PATENT DOCUMENTS

2006/0241564 A1* 10/2006 Corcoran .......... A61M 25/0147 604/523
2008/0249436 A1 10/2008 Darr
(Continued)

FOREIGN PATENT DOCUMENTS

WO WO 2011/046002 A1 4/2011
WO WO 2018/182701 A1 10/2018

OTHER PUBLICATIONS

International Search Report received in International Application No., PCT/EP2022/064460, mailed on Aug. 22, 2022.
(Continued)

*Primary Examiner* — Diane D Yabut
*Assistant Examiner* — Christian D Knauss
(74) *Attorney, Agent, or Firm* — Knobbe, Martens Olson & Bear, LLP

(57) ABSTRACT

A surgical device, including a tubular outer shaft and an inner element having an elongated shape, the outer shaft comprising a distal and a proximal outer hinges, the inner
(Continued)

element comprising an inner hinge, the surgical device having: a first and a second distal stiffnesses considered at the distal outer hinge; and first and second proximal stiffnesses considered at the proximal outer hinge; each of the second distal and proximal stiffnesses being superior to, respectively, the first distal and proximal stiffness; the inner element being able to move angularly and/or axially in the tubular outer shaft, between a first configuration and a second configuration, so that in the first configuration, the surgical device has the second distal stiffness and the first proximal stiffness.

19 Claims, 12 Drawing Sheets

(56) References Cited

U.S. PATENT DOCUMENTS

2011/0230718 A1* 9/2011 Akui .................... A61B 1/0052 600/146
2013/0274784 A1* 10/2013 Lenker ............... A61B 17/3417 606/185
2019/0133705 A1* 5/2019 Riojas .................. A61B 1/0052

OTHER PUBLICATIONS

European Search Report received in European Application No. EP 21 30 5714, dated Nov. 5, 2021.

* cited by examiner

FLEXIBLE SURGICAL DEVICE WITH CONTROLLABLE STIFFNESS

The present invention relates to a surgical device, comprising a tubular outer shaft and an inner element, each of said outer shaft and said inner element having an elongated shape extending along a longitudinal axis between a proximal end and a distal end, the tubular outer shaft comprising at least a distal and a proximal outer hinges, the distal outer hinge being closer to the distal end than the proximal outer hinge; each outer hinge comprising a first and a second outer slits facing each other relative to a first longitudinal plane crossing the outer shaft and parallel to the longitudinal axis of said outer shaft, the inner element comprising at least one inner hinge, the or each inner hinge comprising a first and a second inner slits facing each other relative to a second longitudinal plane crossing the inner element and parallel to the longitudinal axis of said inner element.

Surgical or diagnostical acts, such as biopsies, are carried out by means of percutaneous flexible devices, especially flexible needles.

The effectiveness of the device depends on its ability to follow a controlled curved path during insertion inside biological tissues, such as a human body. In particular, a millimeter-accuracy of the path is needed as the needle may get near vital organs before reaching its target.

In order to achieve a curved path of a flexible surgical device inside tissues, it is known to actively modify a bending of the device during the insertion of the device, with the help of actuators such as cables. Document WO2005/120326 discloses an endoscope with an articulating mechanism, wherein the bending is remotely controlled by means of cables incorporated in the surgical device.

Another approach, known as "passive approach", is based on the interaction of the tissues with the distal end of the surgical device, during its path toward a target. By aid of a radiological or MRI-monitoring, the trajectory of the inserted device is controlled by progressively modifying the stiffness of the distal end. The variable stiffness allows the device to bend, or inversely to pursue a straight path, depending on the tissues/organs nearby.

In particular, document U.S. Pat. No. 8,057,403 discloses a surgical device as detailed above, in particular a biopsy needle, allowing control of a local stiffness of the distal end.

The present invention aims to provide a surgical device allowing a precise and accurate control of the stiffness, for an improved efficiency.

For this purpose, the invention relates to a surgical device of the aforementioned type, wherein: the surgical device has a first and a second distal stiffnesses considered at the distal outer hinge; and a first and a second proximal stiffnesses considered at the proximal outer hinge; each of the second distal and proximal stiffnesses being superior to, respectively, the first distal and proximal stiffness; and the inner element is able to move angularly and/or axially in the tubular outer shaft, between a first configuration and at least a second configuration of the tubular outer shaft and the inner element relative to each other, so that the first and the second distal stiffnesses correspond respectively to a first and to a second positions of the at least one inner hinge relative to the distal outer hinge, and that the first and the second proximal stiffnesses correspond respectively to a first and to a second positions of the at least one inner hinge relative to the proximal outer hinge, the surgical device being configured so that, in the first configuration, the surgical device has the second distal stiffness and the first proximal stiffness.

According to preferred embodiments, the surgical device may include one or more of the following features, considered alone or in any technically possible combination:

- the at least one inner hinge of the inner element is a distal inner hinge; and the inner element also comprises at least a proximal inner hinge, the distal inner hinge being closer to the distal end than the proximal inner hinge;
- the first and second outer slits of the distal and proximal outer hinges face each other relative to a same longitudinal plane crossing the outer shaft, and the first and second inner slits of the distal and proximal inner hinges face each other relative to distinct longitudinal planes (crossing the inner element; or the first and second outer slits of the distal and proximal outer hinges face each other relative to distinct longitudinal planes crossing the outer shaft, and the first and second inner slits of the distal and proximal inner hinges face each other relative to a same longitudinal plane crossing the inner element; or the first and second outer slits of the distal and proximal outer hinges face each other relative to distinct longitudinal planes crossing the outer shaft, and the first and second inner slits of the distal and proximal inner hinges also face each other relative to distinct longitudinal planes crossing the inner element;
- the distal and proximal outer hinges are contiguous; the distal and proximal inner hinges are contiguous; and a distance between the distal and proximal outer hinges is different from a distance between the distal and proximal inner hinges;
- the distance between the distal and proximal outer hinges is equal to a multiple of the distance between the distal and proximal inner hinges;
- the outer shaft also comprises a further outer hinge, the proximal outer hinge being closer to the distal end than the further outer hinge, the surgical device having a first and a second further stiffnesses considered at the further outer hinge; the second further stiffness being superior to the first further stiffness;
- the surgical device is configured so that, in the first configuration, the surgical device has the second distal and further stiffnesses and the first proximal stiffness;
- the inner element also comprises a further inner hinge, the proximal inner hinge (**80*f***) being closer to the distal end than the further inner hinge; the distal and proximal inner hinges are contiguous; the proximal and further inner hinges are contiguous; and a distance between the distal and proximal inner hinges is different from a distance between the proximal and further inner hinges;
- each of the first and second outer slits of at least one outer hinge comprise: a notch extending between two ends; and two curved cuts, each curved cut being connected to one end of the notch;
- the distal end of the outer shaft and/or of the inner element includes a pointed tip;
- the inner element is tubular; and the surgical device also comprises a core element having an elongated shape extending between a proximal end and a distal end, said core element being able to move angularly and/or axially in the inner element;
- the distal end of the core element includes a pointed tip;
- the at least one inner hinge has an axial length superior to an axial length of the outer hinges;
- the axial length of the at least one inner hinge is equal to a multiple of the axial length of the outer hinges;

the inner element comprises at least a pair of contiguous inner hinges and a distance between said pair of contiguous inner hinges is a multiple of the axial length of the outer hinges;

the inner element comprises at least a first and a second inner hinges, at least said first inner hinge having an axial length superior to the axial length of the outer hinges; the inner element is able to move axially in the tubular outer shaft, between a first and a second configurations, a first of the proximal and distal outer hinges are axially level with the first inner hinge in both of said first and second configurations, so that, considered at said first outer hinge, the surgical device has the first stiffness in both of said first and second configurations; and the second of the proximal and distal outer hinges is axially level with the second inner hinge in the first configuration and axially distant from the second inner hinge in the second configuration, so that, considered at said second outer hinge, the surgical device has the first stiffness in the first configuration and the second stiffness in the second configuration;

the inner element is able to move axially, preferably axially and angularly, in the tubular outer shaft, between different configurations of the tubular outer shaft and the inner element relative to each other;

the surgical device also comprises a locking mechanism allowing to lock/unlock an axial position of the inner element relative to the tubular outer shaft.

The invention also relates to a surgical method comprising the following steps insertion into biological tissues of the distal end of the tubular outer shaft of a surgical device as described above; orientation of the distal end toward a target; progressively pushing of the surgical device in the corresponding direction, a path of the distal end being followed by optional medical imaging monitoring; during the path, progressive and local adaptation of the stiffness of the distal end by translating and/or rotating the inner element relative to the tubular outer shaft of the surgical device, in order to allow said distal end to bend, or inversely to pursue a straight path.

The invention will be easier to understand in view of the following description, provided solely as an example, and with reference to the appended drawings, wherein.

Figure 1:
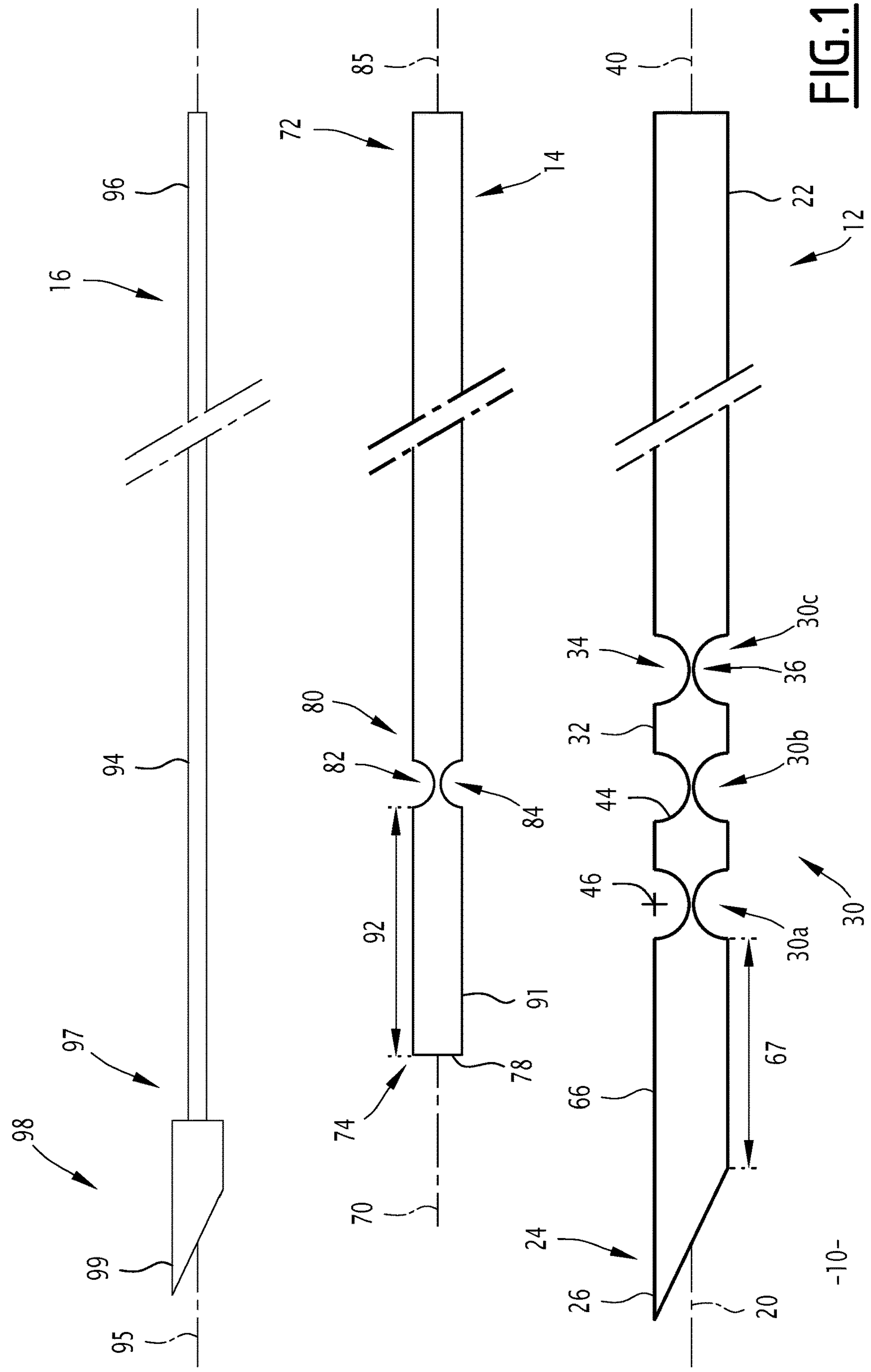
FIG. 1 is a lateral view of a surgical device according to a first embodiment of the invention, in a dissociated configuration.

Each of FIGS. 1-5 shows a surgical device 10, 110, 210, 310, 410 according to a first, a second, a third, a fourth and a fifth embodiments of the invention, respectively.

The surgical devices 10, 110, 210, 310 and 410 will be described simultaneously, the common elements being designed by the same reference numbers.

The surgical device 10, 110, 210, 310, 410 comprises a tubular outer shaft 12, 112, 212, 312, 412 and an inner element 14, 114, 214, 314, 414. In the embodiments of FIGS. 1, 3, 4 and 5, the surgical device 10, 210, 310, 410 also comprises a core element 16 which is not drawn on FIGS. 3 and 4.

The tubular outer shaft 12, 112, 212, 312, 412 of the surgical device 10, 110, 210, 310, 410 will now be described.

The tubular outer shaft 12, 112, 212, 312, 410 has an elongated shape. As described below, the tubular outer shaft is flexible. However, in the following description, the tubular outer shaft is considered in a rectilinear configuration.

The tubular outer shaft 12, 112, 212, 312, 410 extends along a first main axis 20 between a proximal end 22 and a distal end 24. Preferably, the tubular outer shaft 12, 112, 212, 312, 410 has a substantially circular cross-section, centered on the first main axis 20.

In an embodiment, as on FIGS. 1, 3, 4 and 5, the distal end 24 of the tubular outer shaft 12, 212, 312, 412 includes a pointed tip, preferably a bevel tip 26. In another embodiment, as on FIG. 2, the distal end of the tubular outer shaft 112 includes an edge 128 substantially perpendicular to the first main axis 20.

The tubular outer shaft 12, 112, 212, 312, 412 comprises at least two outer hinges 30, 430 distributed along its length.

Figure 2:
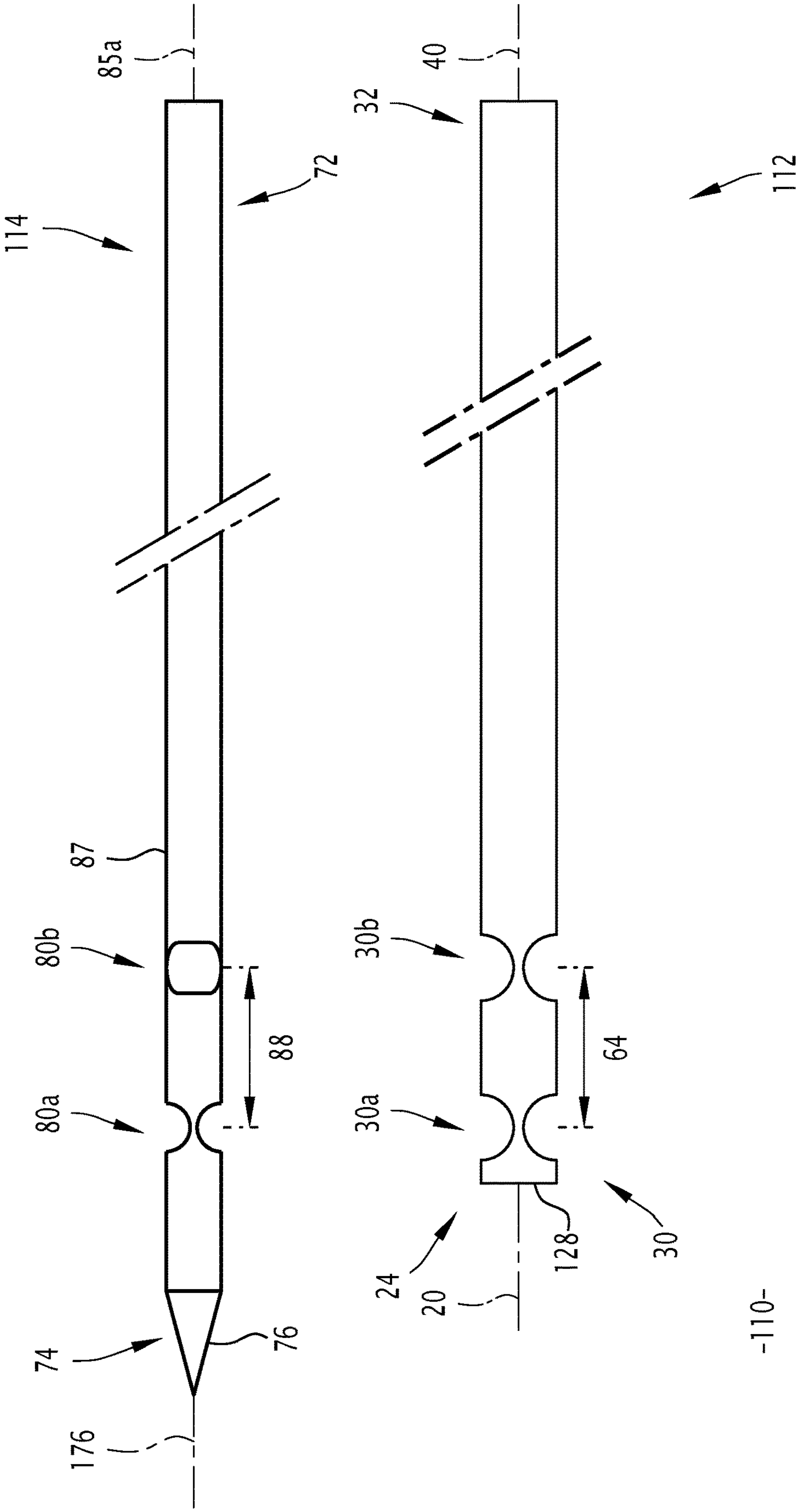
FIG. 2 is a lateral view of a surgical device according to a second embodiment of the invention, in a dissociated configuration.
Figure 3:
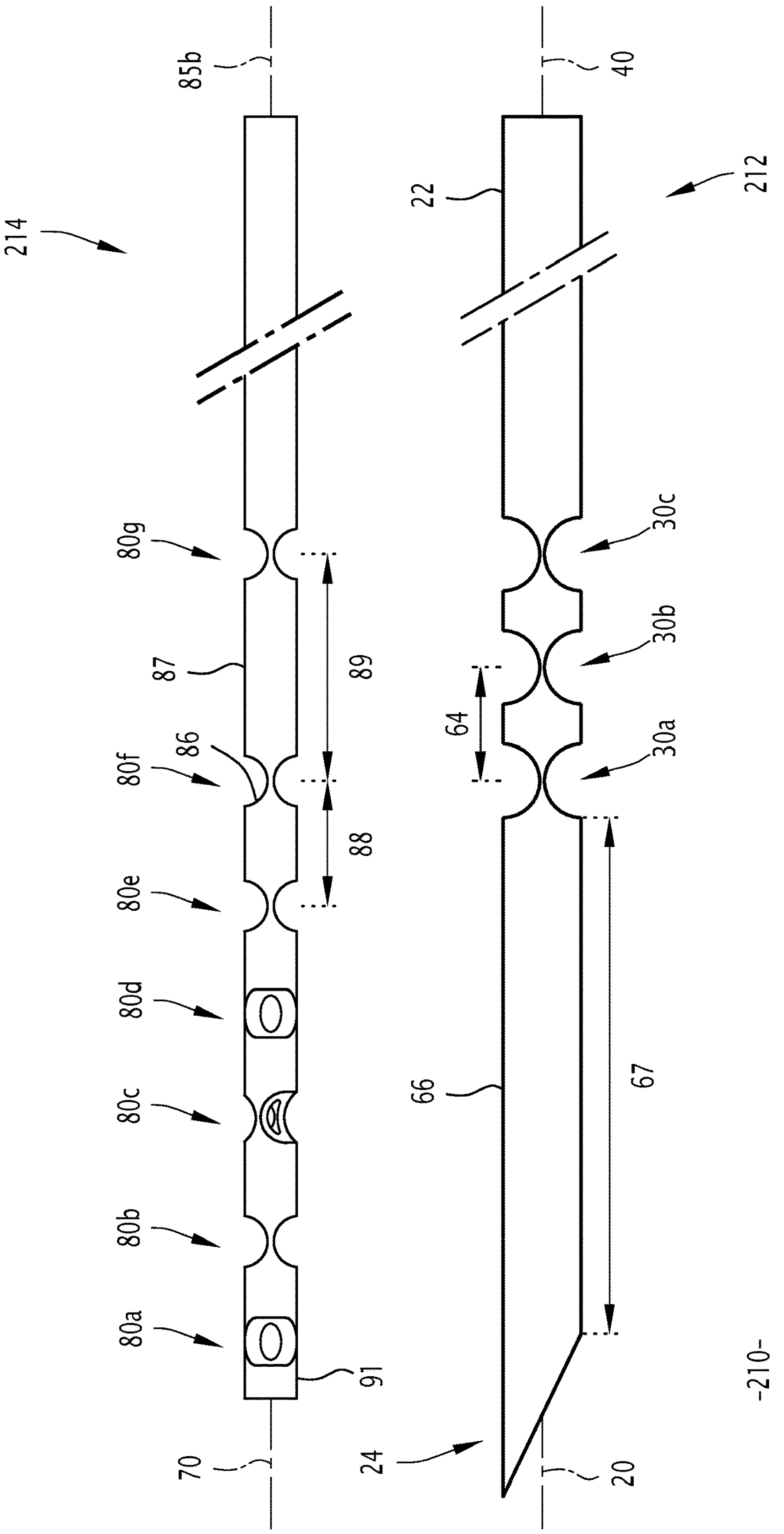
FIG. 3 is a partial, lateral view of a surgical device according to a third embodiment of the invention, in a dissociated configuration.
Figure 4:
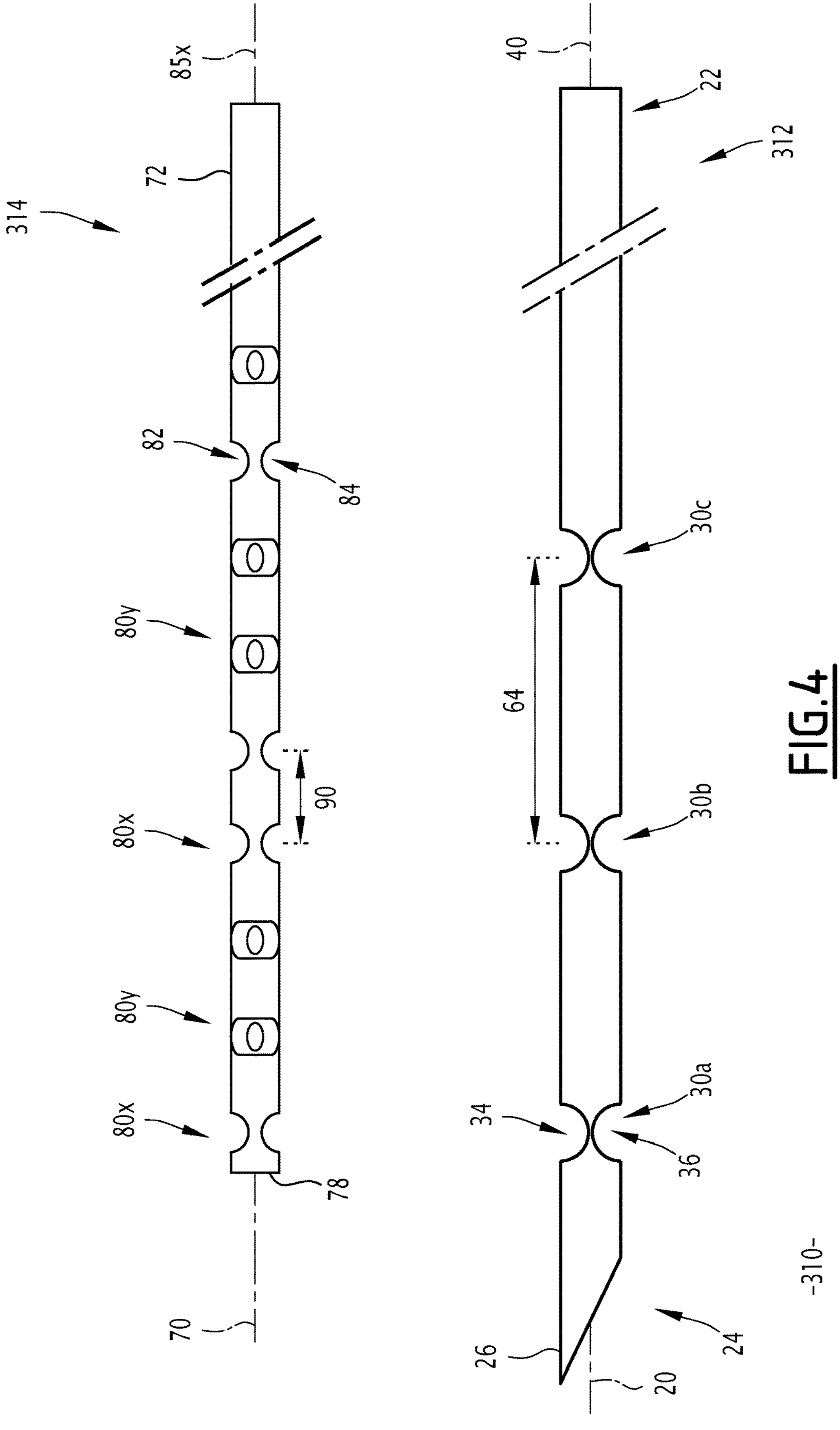
FIG. 4 is a partial, lateral view of a surgical device according to a fourth embodiment of the invention, in a dissociated configuration.

In the embodiment of FIG. 2, the tubular outer shaft 112 comprises two outer hinges 30*a* and 30*b*. In the embodiments of FIG. 1, FIG. 3 and FIG. 4, the tubular outer shaft 12, 212, 312 comprises three successive outer hinges 30*a*, 30*b*, 30*c*. In each embodiment, the outer hinge 30*a* is the closest to the distal end 24.

Figure 6:
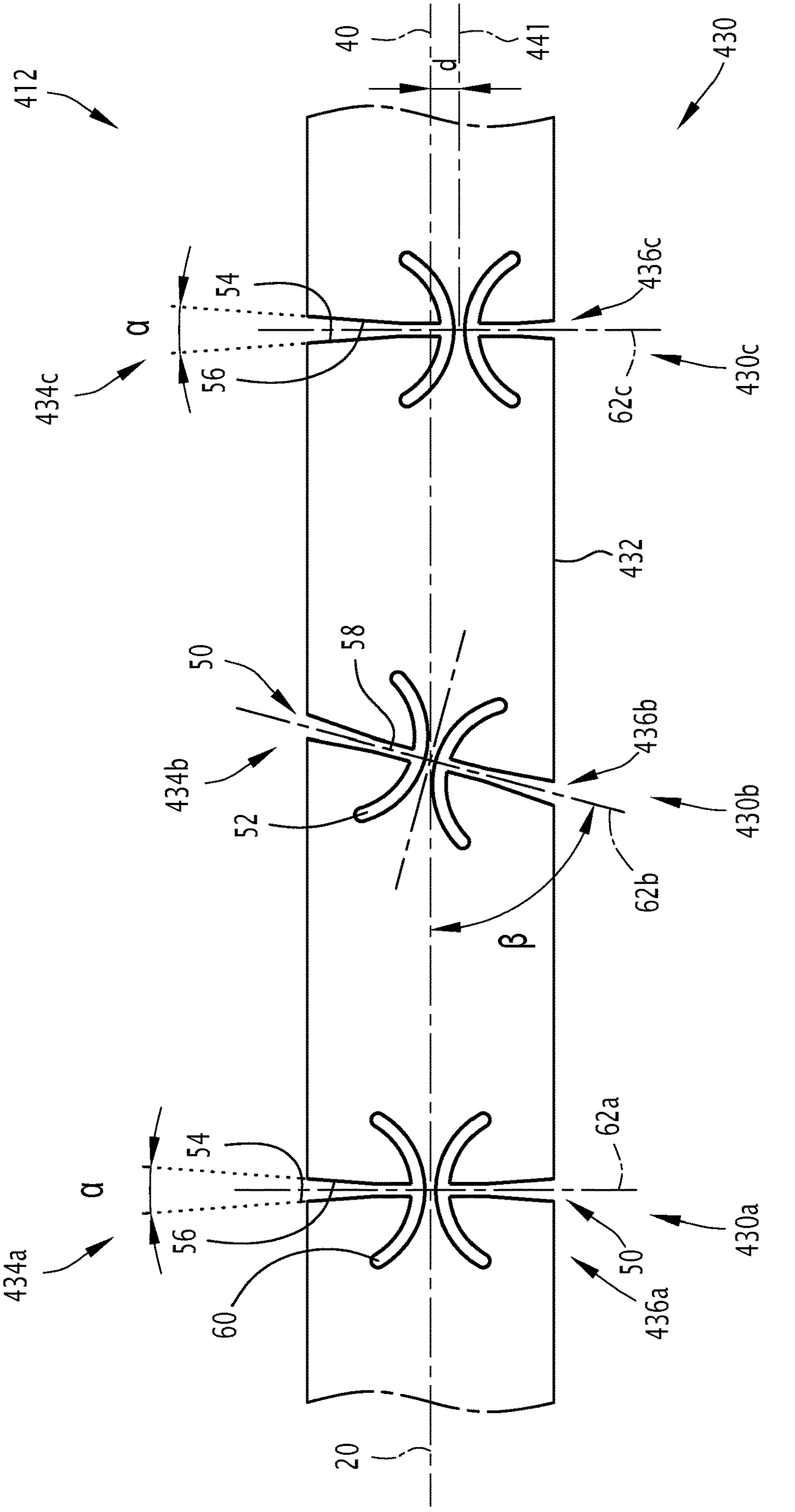
FIG. 6 is a partial, lateral view of the surgical device of FIG. 5.

As shown on FIG. 6, the tubular outer shaft 412 comprises at least three successive outer hinges 430*a*, 430*b*, 430*c*.

According to an embodiment, a same tubular outer shaft 12, 112, 212 comprises identical outer hinges 30. According to another embodiment, a same tubular outer shaft 412 comprises different outer hinges 430*a,b,c*.

Each outer hinge 30, 430 comprises a first 34, 434 and a second 36, 436 outer slits. Said first and second outer slits face each other relative to a longitudinal plane 40, 441 crossing the tubular outer shaft 12, 112, 212, 312, 412. By "longitudinal plane" is meant a plane including the first main axis 20 or parallel to the first main axis 20.

In some embodiments, such as on FIGS. 1-4, the first 34 and second 36 outer slits of each outer hinge 30 face each other relative to a same longitudinal plane 40 crossing the tubular outer shaft 12, 112, 212, 312. Said longitudinal plane 40 includes the first main axis 20. In other terms, said longitudinal plane 40 is a longitudinal median plane of the tubular outer shaft 12, 112, 212, 312.

Figure 5:
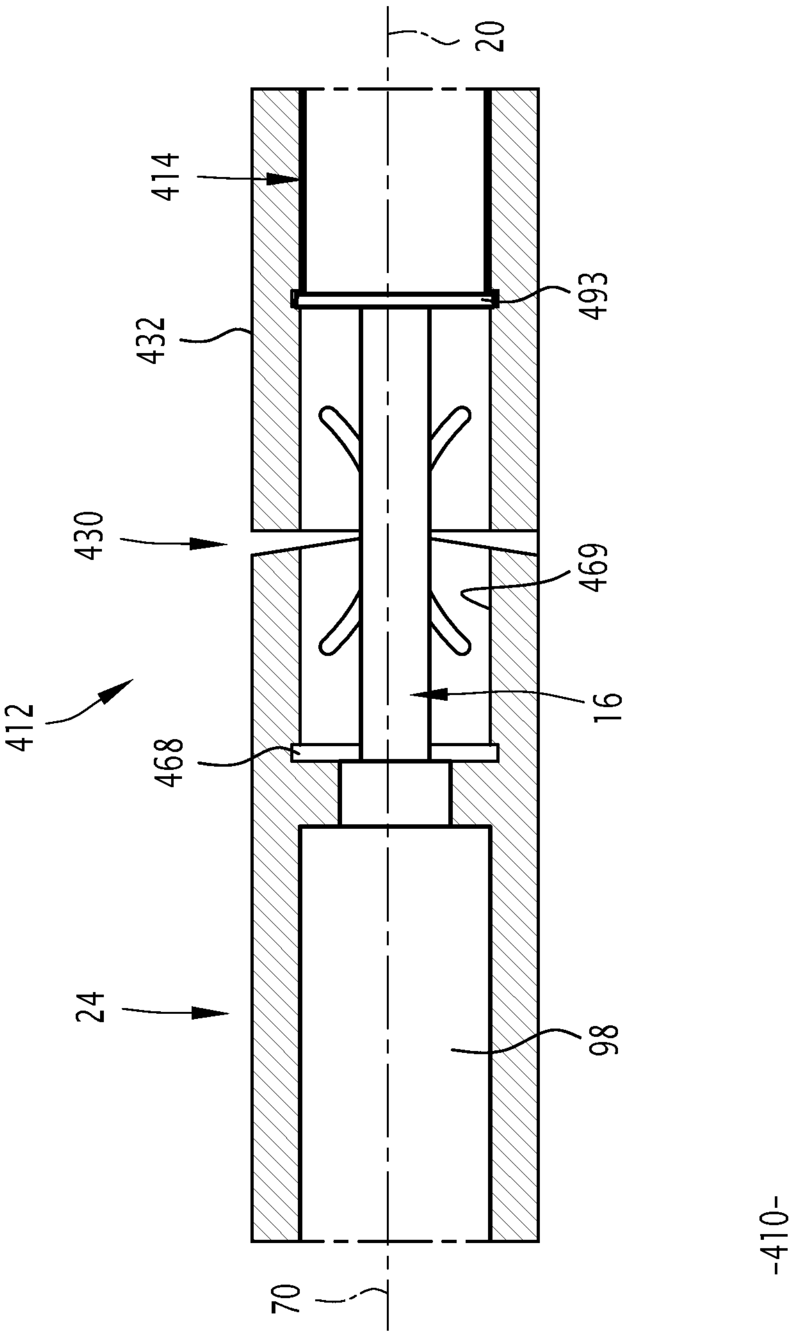
FIG. 5 is a partial, sectional view of a surgical device according to a fifth embodiment of the invention, in an assembled configuration.

In the embodiment of FIGS. 5-6, each of the outer hinges 430*a* and 430*b* comprises a pair of outer slits 434*a*, 436*a*, 434*b*, 436*b* facing each other relative to a first longitudinal plane 40 including the first main axis 20 of the tubular outer shaft 412. The outer hinge 430*c* comprises a pair of outer slits 434*c*, 436*c*, facing each other relative to a second longitudinal plane 441. Said second longitudinal plane is distinct from and parallel to the first longitudinal plane 40. For example, the second longitudinal plane 441 is apart from the first main axis 20 by a non-zero distance d.

In some embodiments, the first 34, 434*a* and second 36, 436*a* outer slits of each outer hinge 30, 430*a* are symmetrical relative to the longitudinal median plane 40 of the tubular outer shaft. On the contrary, the outer slits of each of the outer hinges 430*b* and 430*c* are non-symmetrical relative to any longitudinal median plane of the tubular outer shaft 412.

Each of the first 34, 434 and second 36, 436 outer slits of each outer hinge 30, 430 has a closed contour. In some embodiments, such as on FIGS. 1-3, the closed contour 44 of each of the first 34 and second 36 outer slits has a curved shape. More specifically, the contour 44 corresponds to an intersection of the tubular outer shaft 12, 112, 212, 312 with a revolution cylinder extending along an axis 46 perpendicular to and distant from the first main axis 20.

In other embodiments, such as on FIGS. 4-5, each of the first 434*a*, 434*b*, 434*c* and second 436*a*, 436*b*, 436*c* outer slits of each outer hinge 430*a*, 430*b*, 430*c* has a specific shape, here designed as anchor profile and described below:

The anchor profile comprise a notch 50 and a pair of curved cuts 52. The notch 50 comprises two edges 54, 56 facing each other, each edge being planar. The planes corresponding to the edge 54, 56 of a notch 50 form a first angle α.

The notch 50 extends between two ends 58. Each end is connected to a curved cut 52. The curved cut 52 extends on each side of the corresponding end 58 of the notch, between two closed extremities 60. A concavity of the curved cut is oriented toward the notch 50. Therefore, each curved cut 52, connected to a corresponding end 58 of the notch 50, features an anchor shape.

Preferably, the notches 50 of each of the first 434*a,b,c* and second 436*a,b,c* outer slits of a same outer hinge 430*a,b,c* have a same middle plane 62*a,b,c*. The middle plane 62*a,b,c* is defined as being equidistant to the planes of the edges 54, 56 of each notch 50.

In some embodiments, the middle plane 62*a,c* of the notches 50 of each outer hinge 430*a,c* is perpendicular to the first main axis 20. However, due to the shape of the outer hinge 430*c*, the two notches 50 of said outer hinge display different lengths between their respective ends 58.

In other embodiments, the middle plane 62*b* of the notches 50 of the outer hinge 430*b* is inclined by a second angle β relative to the first main axis 20. The second angle β is strictly inferior to 90°. For example, the second angle β is comprised between 45° and 750.

According to other embodiments (not shown) of the tubular outer shaft, non-symmetrical outer hinges such as the outer hinges 430*b,c* of FIG. 6 have curved closed contours 44 similarly to FIGS. 1-3.

A tubular outer shaft according to the invention may comprise outer hinges displaying other shapes than the shapes described above. A same tubular outer shaft according to the invention may comprise symmetrical outer hinges and/or non-symmetrical outer hinges.

In the embodiments of FIGS. 1-4, the tubular outer shaft 12, 112, 212, 312 comprises two or three outer hinges 30. However, a tubular outer shaft according to the invention may comprise a higher number of outer hinges, such as a number comprised between four and ten, or a much higher number, for example comprised between twenty and a hundred.

Each pair of contiguous outer hinges 30, 430 is axially separated by a section 32, 432 of the tubular outer shaft 12, 112, 212, 312, 412. The section 32, 432 forms a continuous cylindrical surface. A distance 64 between a pair of contiguous outer hinges 30 is considered as a distance along the first main axis 20 between the rotation axes of said outer hinges.

In a same tubular outer shaft 12, 212, 312 comprising at least three outer hinges 30, the distances 64 may be identical or different. In the embodiments shown on FIGS. 1-7, the distances 64 in a same tubular outer shaft are identical.

In the embodiments of FIGS. 1, 3 and 4, wherein the tubular outer shaft 12, 212, 312 includes a pointed tip 26, an end section 66 is comprised between said tip and the outer hinge 30*a* closest to said tip. The end section 66 forms a continuous cylindrical surface having an axial length 67.

In an embodiment, the tubular outer shaft 412 also comprises at least one first locking organ 468, as shown on FIG. 5. The or each first locking organ comprises a groove 468 dug in an inner wall 469 of the tubular outer shaft 412. The groove 468 extends in a plane perpendicular to the first main axis 20. As will be detailed below, the groove 468 has a non-circular shape, for example an elliptical shape.

The tubular outer shaft 412 preferably comprises several first locking organs 468. For example, each section 432 of the tubular outer shaft 412 comprises a first locking organ 468, between two contiguous outer hinges 430.

The inner element 14, 114, 214, 314, 414 of the surgical device 10, 110, 210, 310, 410 will now be described.

The inner element 14, 114, 214, 314, 414 has an elongated shape. As described below, in some embodiments, the inner element is flexible. However, in the following description, the inner element is considered in a rectilinear configuration.

The inner element 14, 114, 214, 314, 414 extends along a second main axis 70 between a proximal end 72 and a distal end 74. Preferably, the inner element 14, 114, 214, 314, 414 has a substantially circular cross-section, centered on the second main axis 70.

The inner element 14, 114, 214, 314, 414 is able to be inserted in the tubular outer shaft 12, 112, 212, 312, 412 of the surgical device 10, 110, 210, 310, 410 according to an assembled configuration such as shown on FIG. 5. In the assembled configuration, the first 20 and second 70 main axes are merged.

As will be detailed below, the inner element 14, 114, 214, 314, 414 is able to move angularly and/or axially in the tubular outer shaft 12, 112, 212, 312, 412 of the surgical device 10, 110, 210, 310, 410.

In an embodiment, such as on FIG. 2, the inner element 114 is non-tubular and has a full core. In other embodiments, such as on FIG. 1 and FIGS. 3-5, the inner element 14, 214, 314, 414 is tubular.

In an embodiment, such as on FIG. 2, the distal end 74 of the inner element 14 includes a pointed conical tip 176. According to another embodiment (not shown), the distal end of the inner element includes a bevel tip.

In other embodiments, such as on FIG. 1 and FIGS. 3-5, the distal end 74 of the tubular inner element includes a flat edge 78.

The inner element 14, 114, 214, 314, 414 comprises at least one inner hinge 80. Preferably, the inner element comprises at least two, and more preferably a plurality of inner hinges 80 distributed along its length.

In the embodiment of FIG. 1, the inner element 14 comprises a single inner hinge 80. In the embodiment of FIG. 2, the inner element 114 comprises two inner hinges 80*a* and 80*b*. In the embodiment of FIG. 3, the inner element 214 comprises seven inner hinges 80*a-g*. Similarly, in the embodiment of FIG. 4, the inner element 314 comprises nine inner hinges 80. In the embodiments of FIGS. 2 and 3, the inner hinge 80*a* is the closest to the distal end 74.

An inner element according to the invention may comprise number of inner hinges comprised between three and ten, or a much higher number, for example comprised between twenty and a hundred. Moreover, the number, position and/or orientation of inner hinges may be different from the number, position and/or orientation of outer hinges of a same surgical device.

Each inner hinge 80 comprises a first 82 and a second 84 inner slits. Said first and second inner slits face each other relative to a longitudinal plane 85 crossing the inner element 14, 114, 214, 314, 414. By "longitudinal plane" is meant a plane including the second main axis 70 or parallel to the second main axis 70.

Preferably, said longitudinal plane 85 includes the second main axis 70; in other terms, said longitudinal plane 85 is a longitudinal median plane of the inner element 14.

In an embodiment (not shown) wherein the inner element comprises at least two inner hinges 80, the first 82 and second 84 inner slits of each inner hinge face each other relative to a same longitudinal plane crossing the inner element.

In others embodiments, such as on FIGS. 2, 3 and 4, the longitudinal planes of the inner hinges 80 have at least two different orientations.

More specifically, in the embodiment of FIG. 2, the longitudinal planes of the inner hinges 80*a* and 80*b* are perpendicular to each other. The longitudinal plane 85*a* of the inner hinge 80*a* is shown on FIG. 2.

Similarly, in the embodiment of FIG. 4, the inner hinges 80 of the inner element 314 form two groups 80*x* and 80*y*, the inner hinges of a same group having a same longitudinal plane, the longitudinal planes of the two groups being perpendicular to each other. The longitudinal plane 85*x* of the inner hinges 80*x* is shown on FIG. 4.

In the embodiment of FIG. 3, the longitudinal planes of the inner hinges 80*a-g* have more than two different orientations. For example, as shown on FIG. 7, the longitudinal planes 85*b*, 85*c* and 85*d* of the successive inner hinges 80*b*, 80*c* and 80*d* intersect along the second main axis 70 and are inclined by third angles $\gamma$ relative to each other, forming a helical pattern. The third angles are superior to zero.

Figure 7:
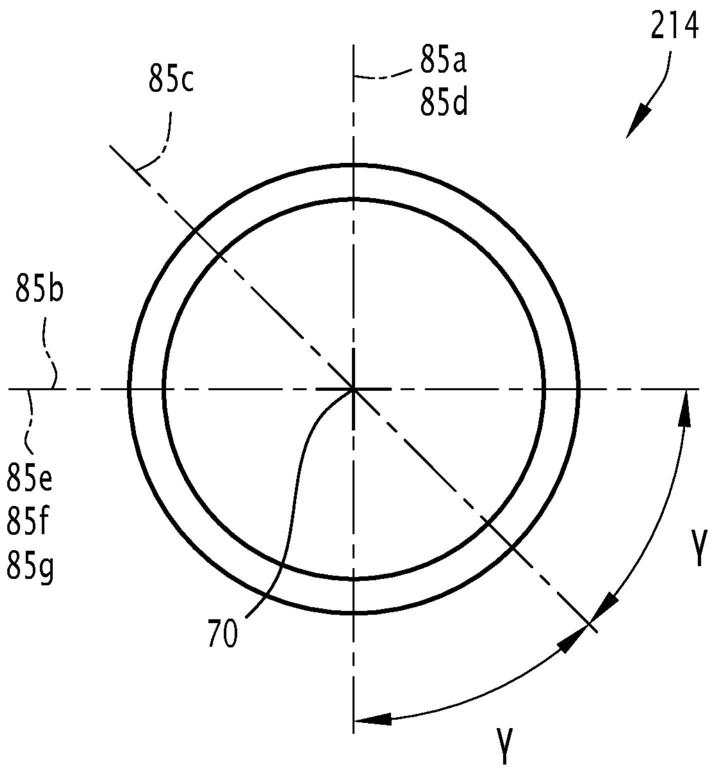
FIG. 7 is a partial front view of the surgical device of FIG. 3.

Preferably, the third angle $\gamma$ formed by two adjacent longitudinal planes 85*b*, 85*c* and 85*c*, 85*d* is comprised between 10° and 60°. In the embodiment of FIGS. 3 and 7, the third angle $\gamma$ is equal to 45°. The longitudinal planes 85*b* and 85*d* are perpendicular to each other.

In the embodiment of FIG. 3, the longitudinal plane 85*a* of the inner hinge 80*a* is merged with the longitudinal plane 85*d*; and each of the longitudinal planes 85*e*, 85*f* and 85*g* of the inner hinges 80*e,f,g* is merged with the longitudinal plane 85*b*.

A disposition of the hinges with different angular orientations may also be used for the outer hinges of the tubular outer shaft described above.

In the embodiments of FIGS. 1-4, the first 82 and second 84 inner slits of each inner hinge 80 are symmetrical relative to the corresponding longitudinal plane 85. According to other embodiments (not shown), the inner element may include non-symmetrical inner hinges, similarly to the non-symmetrical outer hinges 430*b* and 430*c* of the tubular outer shaft 412 described above.

Preferably, each of the first 82 and second 84 inner slits of each inner hinge 80 has a closed contour 86. In the embodiments of FIGS. 1-4, the closed contour 86 has a curved shape, similarly to the outer hinges 30 described above. According to other embodiments (not shown), the inner hinges may have different shapes, such as the anchor profiles described above for the outer hinges 430 of the tubular outer shaft 412.

In an alternative embodiment of FIG. 2 (not shown), the non-tubular inner element comprises inner hinges in the shape of circular grooves, instead of a pair of opposite inner slits. Each circular groove extends in a plane perpendicular to the second main axis 70. The circular grooves surround an inner core extending along the second main axis 70.

Preferably, with the exception of the at least one inner hinge 80, the inner element 14, 114, 214, 314, 414 forms a continuous cylindrical surface 87. In the embodiments comprising more than one inner hinge 80, a distance 88, 89, 90 between a pair of contiguous inner hinges 80 is considered as a distance along the second main axis 70 between the rotation axes of said inner hinges.

In an embodiment, such as on FIGS. 2 and 3, a distance 88 between at least one pair of contiguous inner hinges 80 is equal to the distance 64 between a pair of contiguous outer hinges 30. In other terms, it is possible to place each of said contiguous inner hinges 80 in axial level with one outer hinge 30, as explained below.

In a same inner element 214, 314 comprising at least three outer hinges 80*a-g*, 80*x-y*, the distances 88, 89, 90 may be identical or different. In the embodiment of FIG. 3, the distance 89 between the contiguous inner hinges 80*f* and 80*g* is superior to the distance 88 between each other pair of contiguous inner hinges. More specifically, the distance 89 is equal to twice the distance 88. In the embodiment of FIG. 4, the contiguous inner hinges 80*x,y* are separated by a same distance 90.

In an embodiment, such as on FIG. 4, the distance 64 between a pair of contiguous outer hinges 30 is equal to a multiple of a distance 90 between a pair of contiguous inner hinges 80. In other terms, when each of two contiguous outer hinges 30 is in axial level with one inner hinge 80, one or more inner hinges are placed between said contiguous outer hinges 30. By "a multiple of", it is understood that 64 is equal to k90, with k being a non-zero natural number, preferably superior or equal to 2.

More specifically, in the embodiment of FIG. 4, the distance 90 between a pair of contiguous inner hinges 80 of the inner element 314 is equal to a third of the distance 64 between a pair of contiguous outer hinges 30*a*, 30*b* and 30*b*, 30*c*.

In the same manner, in the embodiment of FIG. 3, the distance 89 between the contiguous inner hinges 80*f* and 80*g* is different from the distance 64 between a pair of contiguous outer hinges 30, and more specifically equal to twice the distance 64.

An end section 91 is comprised between the distal end 74 of the inner element and the inner hinge 80, 80*a* closest to said distal end. The end section 91 forms a continuous cylindrical surface having an axial length 92.

The inner element 414 of FIG. 5 comprises at least one inner hinge (not shown) and is for example similar to the inner element 14 of FIG. 1.

In an embodiment, the inner element 414 also comprises a second locking organ 493, as shown on FIG. 5. The second locking organ comprises a crown 493 angularly extending from the distal end 74 of the inner element 414. The crown 493 extends in a plane perpendicular to the second main axis 70. The crown 493 has a non-circular shape, for example an elliptical shape, complementary to the shape of the groove 468 of the first locking organ.

The first locking organs 468 of the tubular outer shaft 412 and the second locking organ 493 of the inner element 414 form a locking mechanism, which will be further described.

The core element 16 of the surgical device 10, 210, 310, 410 will now be described.

The core element 16 has an elongated shape. As described below, the core element is flexible. However, in the following description, the core element is considered in a rectilinear configuration.

The core element 16 comprises a body 94 extending along a third main axis 95 between a proximal end 96 and a distal end 97. The body 94 has a cylindrical shape, preferably with a circular cross-section.

The core element 16 also comprises a head 98 adjacent to the distal end 97 of the body. Preferably, the head 98 comprises a pointed tip, such as a bevel tip 99 or a conical tip.

The body 94 of the core element 16 is able to be inserted in the tubular inner element 14, 214, 314 of the surgical device 10, 210, 310 according to an assembled configuration such as shown on FIG. 4. In the assembled configuration, the second 70 and third 95 main axes are merged.

In the embodiments of FIG. 1 and FIGS. 3-5, the head 98 is designed for distally standing out of the tubular inner element 14, 214, 314, 414 in the assembled configuration. However, the head 98 is able to be received inside the tubular outer shaft 12, 212, 312, 412 in said assembled configuration.

As will be detailed below, the body 94 of the core element 16 is able to move angularly and/or axially in the tubular inner element 14, 214, 314, 414 of the surgical device 10, 210, 310, 410.

The surgical device 10, 110, 210, 310, 410 in the assembled configuration is now considered. In said assembled configuration, the inner element 14, 114, 214, 314, 414 is received in the tubular outer shaft 12, 112, 212, 312, 412. In the embodiments of FIGS. 1, 3, 4 and 5, the core element 16 is also received in the tubular inner element 14, 214, 314, 414 in the assembled configuration of the surgical device.

The surgical device 10, 110, 210, 310, 410 is designed so that a local stiffness of said surgical device can be modified in a controlled manner. By “local stiffness”, it is meant a stiffness considered at a specific outer hinge 30, 430 of the tubular outer shaft 12, 112, 212, 312, 410.

More specifically, the local stiffness is modified in a controlled manner by angularly and/or axially moving the inner element 14, 114, 214, 314, 414 in the tubular outer shaft 12, 112, 212, 312, 412. A first and a second positions of the inner element, relative to the tubular outer shaft, correspond respectively to a first and to a second local stiffnesses of the surgical device, the second local stiffness being superior to the first local stiffness.

For example, in the embodiments of FIGS. 1-4, a position of the inner hinge 80, or of one of the inner hinges 80, of the inner element 14, 114, 214, 314, is considered relative to one of the outer hinges 30*i* of the tubular outer shaft 12, 112, 212, 312. Different positions A, B, C are shown on FIG. 8.

A position A corresponds to the inner hinge 80 being at a same axial position as the considered outer hinge 30*i*, and each inner slit 82, 84 angularly facing one of the corresponding outer slit 34, 36 of said outer hinge. In other terms, in the position A, the longitudinal median plane 85 of the inner hinge 80 and the longitudinal median plane 40 of the outer hinge 30*i* are merged.

A position B corresponds to the inner hinge 80 being at a same axial position as the considered outer hinge 30*i* and the longitudinal median plane 85 of the inner hinge 80 is inclined by a non-zero angle relative to the longitudinal median plane 40 of the outer hinge 30*i*.

A position C corresponds to the inner hinge 80 being at a different axial position as the considered outer hinge 30*i*, and said considered outer hinge 30*i* facing the continuous cylindrical surface 87 of the inner element.

In position A of the inner hinge 80, a minimal stiffness of the surgical device is obtained at the considered outer hinge 30*i* of the tubular outer shaft. In other terms, the surgical device 10, 110, 210, 310, 410 is able to bend on each side of the longitudinal median plane 40 of the considered outer hinge 30*i*, with a maximal amplitude.

In position B of the inner hinge 80, a higher stiffness of the surgical device is obtained at the considered outer hinge 30*i* of the tubular outer shaft. The bending amplitude is lower than in position A.

Figure 8:
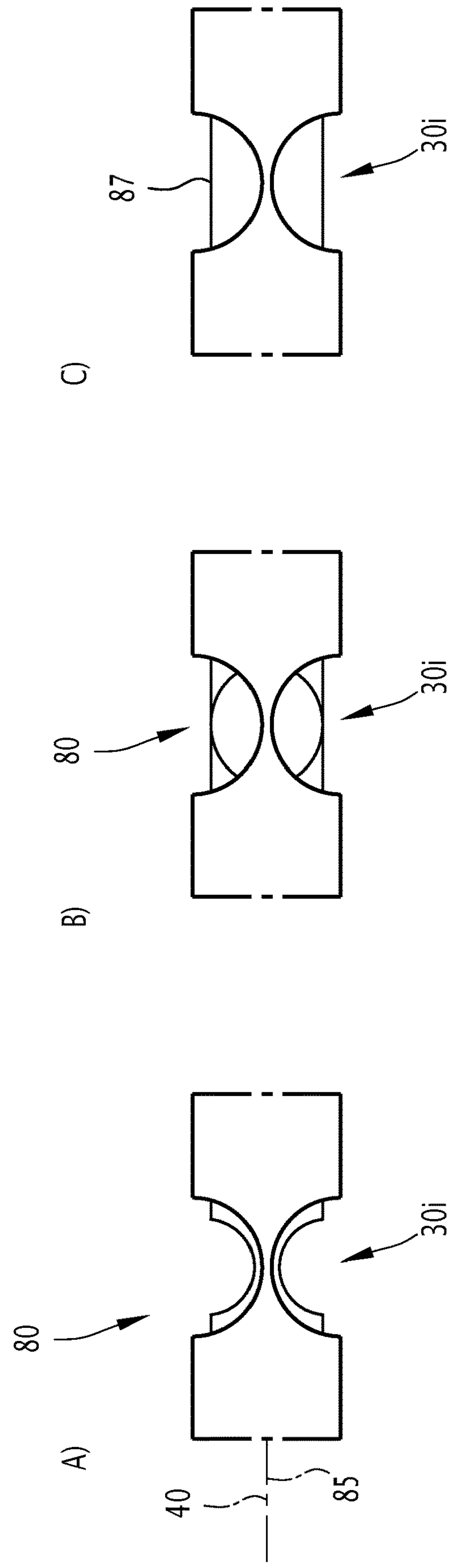
FIG. 8 is a partial, lateral view of surgical devices according to the invention, in assembled configurations.

In the example of FIG. 8, in position B, the longitudinal median plane 85 of the inner hinge 80 is perpendicular to the longitudinal median plane 40 of the outer hinge 30*i*. However, in an alternative position B, the longitudinal median plane 85 of the inner hinge 80 may be inclined by any angle, strictly superior to zero, relative to the longitudinal median plane 40 of the outer hinge 30*i*. The stiffness obtained in position B may be variated continuously in function of the inclination angle between the planes 40 and 85.

In position C of the inner hinge 80, a maximal stiffness of the surgical device is obtained at the considered outer hinge 30*i* of the tubular outer shaft. The bending amplitude is lower than in positions A and B.

The positions A, B and C may be successively obtained at a same outer hinge 30*i*, by axially translating and/or rotating the inner element 14, 114, 214, 314, 414 relative to the tubular outer shaft 12, 112, 212, 312, 412.

Such a property of the surgical device 10, 110, 210, 310, 410 allows a local adaptation of the stiffness, for example during a path of said device toward a target in a patient’s body.

More specifically, the surgical device 10, 110, 210, 310, 410 of the invention allows a combinatorial approach of the stiffness modulation of the outer hinges 30*i* of the tubular outer shaft 12, 112, 212, 312, 412.

In order to explain such a combinatorial approach, a first and a second states of each outer hinge 30*i* are considered, corresponding to a first and to a second stiffness respectively. The second stiffness is superior to the first stiffness.

According to different embodiments, the first and second states may correspond to positions A and B, or to positions A and C, or to positions B and C respectively.

When a outer hinge 30*i* is in the first state, corresponding to the first, lower stiffness, the hinge is considered as “activated”. When an outer hinge 30*i* is in the second state, corresponding to the second, higher stiffness, the hinge is considered as “blocked”.

For a better comprehension of the following, a binary code is attributed, “1” for the first, activated state and “0” for the second, blocked state.

A surgical device of the invention is considered, with a tubular outer shaft comprising a number $n \geq 2$ of outer hinges 30. If each of the outer hinges can be either in the first, activated state or in the second, blocked state, $2^n$ configurations of the surgical device are possible.

In a preferred embodiment, the tubular outer shaft of the surgical device comprises at least two outer hinges, each of the outer hinges being able to be either in the first, activated state or in the second, blocked state. Therefore, at least two configurations of the surgical device are possible.

In another preferred embodiment, the tubular outer shaft of the surgical device comprises at least three outer hinges, at least two of said outer hinges being independently able to be either in the first, activated state or in the second, blocked state. More preferably, each of the outer hinges is able to be either in the first, activated state or in the second, blocked state. Therefore, at least four configurations of the surgical device are possible.

Figure 9:
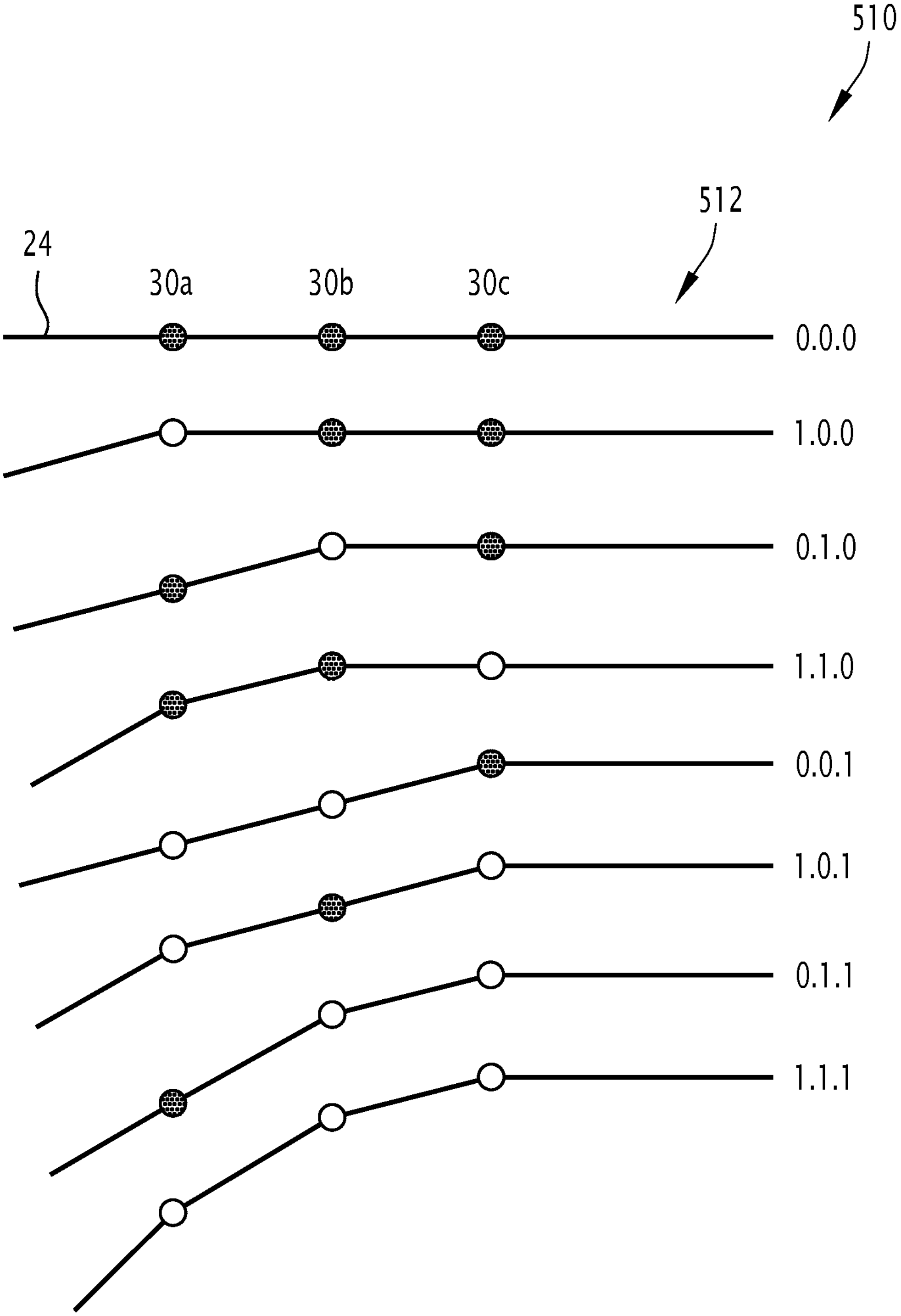
FIG. 9 is a schematic view of different states of a surgical device according to the invention.

The example of FIG. 9 illustrates the possible configurations of a surgical device 510, schematically represented in an assembled configuration, with a tubular outer shaft 512 comprising three outer hinges 30*a*, 30*b* and 30*c* aligned from the distal end 24. The tubular outer shaft 512 is similar to the tubular outer shafts 12, 212, 312 of FIGS. 1, 3 and 4.

For each outer hinge 30*i*, the first, activated state "1" is represented by a white circle and the second, blocked state "0" is represented by a dark circle.

As seen on FIG. 9, eight configurations are possible for the surgical device 510, depending on the activated "1" or blocked "0" state of each outer hinge 30*i*.

In the embodiment of FIG. 1, a purely translative displacement of the inner element 14 relative to the tubular outer shaft 12 allows to obtain several of the above-mentioned eight configurations.

The totally blocked configuration "0.0.0" is obtained by positioning the inner hinge 80 of the inner element 14 between the outer hinge 30*a* and the distal end 24 of the tubular outer shaft 12. The axial lengths 67, 91 of the end sections 66, 90 allow such a positioning with the distal end 74 of the inner element 14 received in the tubular outer shaft 12.

More specifically, in the totally blocked configuration "0.0.0", the position of the inner element 14 relative to each of the outer hinges 30*i* corresponds to the position C of FIG. 8.

By translating the inner hinge 80 of the inner element 14 toward the proximal end 22 of the tubular outer shaft, the configurations "1.0.0", "0.1.0" and "0.0.1" are successively obtained. In the activated state "1" of each of the outer hinges 30*i*, the position of the inner element 14 relative to the considered outer hinge 30*i* corresponds to the position A of FIG. 8, for a minimal stiffness, or alternatively to position B.

When the distal end 74 of the inner element 14 is situated between an outer hinge 30*i* and the proximal end 22 of the tubular outer shaft 12, said outer hinge is also considered in the activated state "1". In this manner, pursuing the translation of the inner hinge 80 of the inner element 14 toward the proximal end 22 allows to successively obtain the configurations "1.0.0" (already obtained above), "1.1.0" and "1.1.1".

Therefore, the embodiment of FIG. 1 allows to obtain six of the eight configurations listed on FIG. 9.

In the embodiment of FIG. 2, it is possible to place each of the inner hinges 80*a*, 80*b* of the inner element 114 facing an outer hinge 30*a*, 30*b* of the tubular outer shaft 112. Therefore, a purely rotative displacement of the inner element 114 relative to the tubular outer shaft 112 allows to obtain two configurations "1.0" and "0.1". In said configurations, the activated state "1" and the blocked state "0" of each of the outer hinges 30*a*, 30*b* correspond to positions A and B of FIG. 8, respectively.

A totally blocked configuration "0.0" may also be obtained by translating the inner element 114 relative to the tubular outer shaft 112 so as to place the inner hinge 80*a* between the outer hinges 30*a* and 30*b*, corresponding to a position C on each of the outer hinges.

In the embodiment of FIG. 3, the large number of inner hinges 80*a-g* allows to obtain many configurations of the surgical device 210, including several of the configurations of FIG. 9.

More specifically, as the distance 89 between the contiguous inner hinges 80*f* and 80*g* is equal to twice the distance 64 between a pair of contiguous outer hinges 30, the configuration "1.0.1" is obtained by placing the inner hinges 80*f* and 80*g* axially level with the outer hinges 30*a* and 30*c* respectively. In the same manner, the configuration "1.1.0" is obtained by placing the inner hinges 80*e* and 80*f* axially level with the outer hinges 30*a* and 30*b* respectively.

The configuration "0.1.1" is obtained by placing the inner hinges 80*d*, 80*e* and 80*f* axially level with the outer hinges 30*a*, 30*b* and 30*c* respectively, with the position B at the outer hinge 30*a* and the position A at the outer hinges 30*b* and 30*c*.

The surgical device 210 of FIG. 3 is now considered with the helically disposed inner hinges 80*b*, 80*c* and 80*d* axially level with the outer hinges 30*a*, 30*b* and 30*c* respectively.

By rotating the inner element 214 relative to the tubular outer shaft 212, the stiffness at each of the outer hinges 30*a,b,c* may be continuously variated in a sinusoidal manner, with a shift of 45° between the stiffnesses of each pair of contiguous outer hinges. For example, when the inner element 214 is in position A relative to the middle outer hinge 30*b*, each of the longitudinal planes 85*b* and 85*d* of the inner hinges 80*b* and 80*d* forms an angle of 45° with the longitudinal plane 40 of the tubular outer shaft 212.

A similar configuration, with a shift of 90° between the stiffnesses of the outer hinges 30*a* and 30*b*, is obtained by placing the inner hinges 80*a*, 80*b* and 80*c* axially level with the outer hinges 30*a*, 30*b* and 30*c* respectively.

In the embodiment of FIG. 4, the inner hinges 80*x* and 80*y* alternate in a non-periodic pattern along the inner element 314. Several of the configurations of FIG. 9 can be successively obtained by combining rotations of 90° and translations of a length of once, twice or three times the distance 90 between two contiguous inner hinges 80. Therefore, this embodiment gives access to a large number of combinations through limited translation lengths of the inner element 314.

In said configurations, the activated state "1" and the blocked state "0" of each of the outer hinges 30 correspond to positions A and B of FIG. 8, respectively.

The surgical device of the invention, with a suitable design of the tubular outer shaft and inner element, allows to obtain any of the $2^n$ possible stiffness configurations, depending on the number n of outer hinges.

In particular, the surgical device of the invention allows to obtain configurations that are not allowed by the devices of the prior art.

For example, it is possible to put a distally placed outer hinge in the second, blocked state "0" and a more proximally placed outer hinge in the first, activated state "1". The combinations "0.1.1", "0.1.0" and "0.0.1", described above, illustrate such a possibility.

Figure 10:
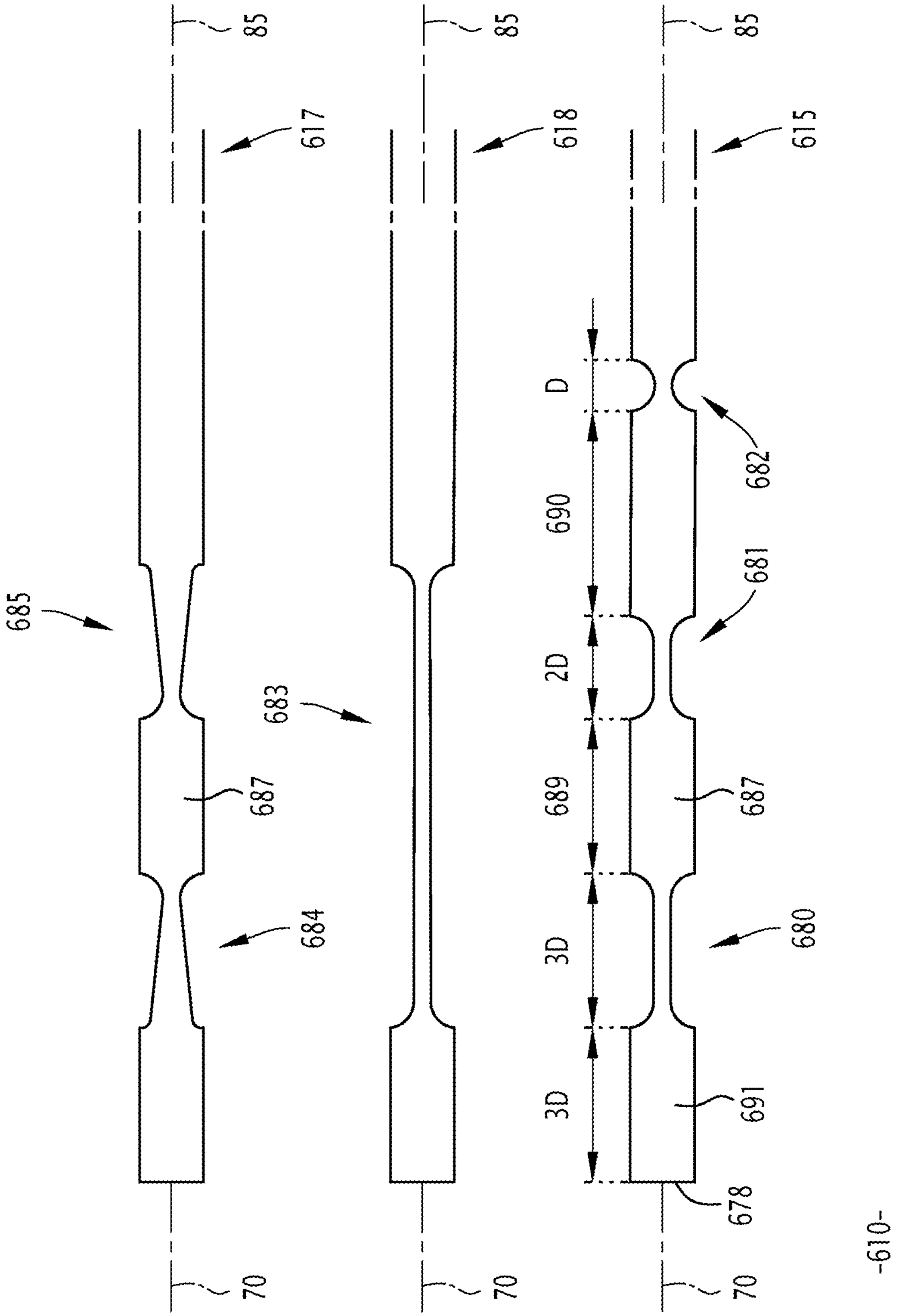
FIG. 10 is a partial, lateral view of a surgical device according to a sixth embodiment of the invention, in a dissociated configuration.
Figure 10:
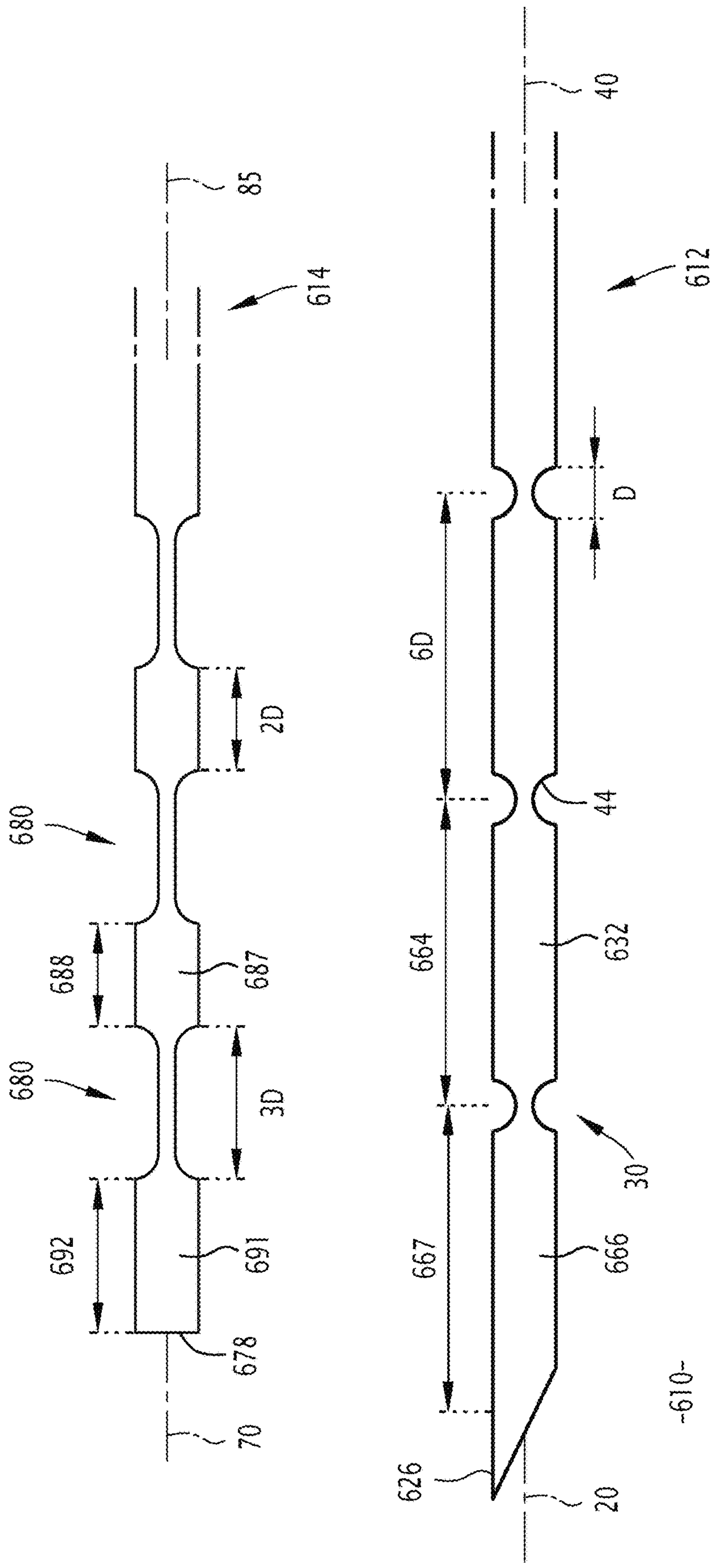
Figure 11:
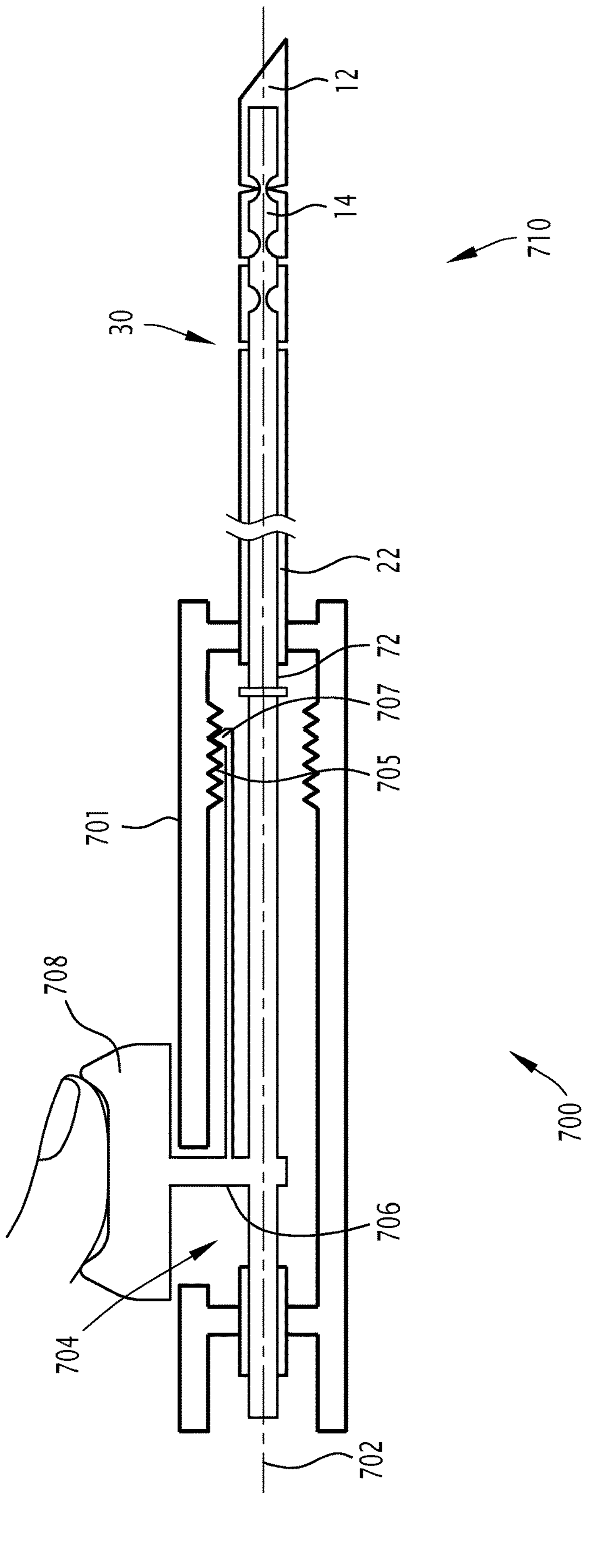
FIG. 11 is a schematic view of an example of a control handle connected to a proximal end of a surgical device, according to one embodiment.

FIG. 10 shows a surgical device 610 according to a sixth embodiment of the invention.

The surgical device 610 comprises: a tubular outer shaft 612; an inner element 614, 615, 616, 617; and a core element 16. Said core element 16, not shown, is described above. Several embodiments 614, 615, 616 and 617 of the inner element are shown on FIG. 10.

The tubular outer shaft 612 is similar to the tubular outer shafts 12, 112, 212, 312, 412 described above. In particular, the tubular outer shaft 612 has an elongated shape extending along a first main axis 20, with a substantially circular cross-section centered on said first main axis. The tubular outer shaft 612 comprises at least two outer hinges 30, preferably at least three outer hinges 30, distributed along its length.

In the embodiment, the tubular outer shaft comprises three outer hinges 30, similar to the outer hinges 30 of the embodiments 12, 112, 212, 312 described above. In an alternative embodiment (not shown), the outer hinges of the tubular outer shaft 612 have the anchor profile shown on FIGS. 5-6.

Each of the outer hinges 30 of the tubular outer shaft 612 comprises a pair of outer slits, as described above. The outer slits are symmetrical relative to a longitudinal median plane 40 of the tubular outer shaft.

The outer hinges 30 of the tubular outer shaft 612 are identical. As described above, the contour 44 of each outer slit corresponds to an intersection of the tubular outer shaft 612 with a revolution cylinder extending along an axis perpendicular to and distant from the first main axis 20. Said revolution cylinder has a diameter D. Each of the outer slits of each inner hinge 30 has an axial length equal to D.

Each pair of contiguous outer hinges 30 is axially separated by a section 632 of the tubular outer shaft 612. The section 632 forms a continuous cylindrical surface.

A distance 664 between a pair of contiguous outer hinges 30 is considered as a distance along the first main axis 20 between the rotation axes of said outer hinges. In the present embodiment, the distance 664 is a multiple of the axial length D. More precisely, in the embodiment of FIG. 10, the distance 664 is equal to 6D.

In the embodiment of FIG. 10, the distal end of the tubular outer shaft 612 includes a pointed tip 626, especially a bevel tip. An end section 666 is comprised between said tip and the outer hinge 30 closest to said tip. The end section 666 forms a continuous cylindrical surface having an axial length 667.

In the present embodiment, the axial length 667 is a multiple of the axial length D. More precisely, in the embodiment of FIG. 10, the axial length 667 is equal to 6D, as the distance 664.

The inner element 614, 615, 616, 617 is similar to the inner elements 14, 114, 214, 314, 414 described above. In particular, the inner element 614, 615, 616, 617 has an elongated shape extending along a second main axis 70, with a substantially circular cross-section centered on said second main axis. The inner element 614, 615, 616, 617 comprises at least one inner hinge 680, 681, 682, 683, 684, 685, preferably at least two or three inner hinges 680, 681, 682, 683, 684, 685 distributed along its length.

Similarly to the inner hinges 80 described above, each of the inner hinges 680, 681, 682, 683, 684 of the inner element 614, 615, 616, 617 comprises a pair of inner slits, symmetrical relative to a longitudinal median plane 85 of the inner element. Each of the inner slits of an inner hinge 680, 681, 682, 683, 684, 685 has a closed contour.

In the embodiments of FIG. 10, at least one of the inner hinges 680, 681 of the inner element 614, 615, 616, 617 has an axially elongated shape. More specifically, each of the inner slits of an inner hinge 680, 681, 683, 684, 685 has an oblong shape, extending along the second main axis 70. An axial length of said inner slits is superior to the axial length D of the outer hinges 30 of the tubular outer shaft 612.

In a first 614, a second 615 and a third 616 embodiments of the inner element, each of the inner slits of the inner hinges 680, 681, 683 is substantially symmetrical according to a plane perpendicular to the second main axis 70.

In a fourth embodiment 617 of the inner element, each of the inner slits of the inner hinges 684 and 685 have a variable depth along the second main axis 70, said depth being considered perpendicularly to the second longitudinal plane 85.

Preferably, the depth of the inner slits varies regularly along the second main axis 70. In an inner hinge 684, the depth of the inner slits increases from the distal end to the proximal end of the inner element 617, from a shallowest end to a deepest end. In another inner hinge 685, the depth of the inner slits decreases from the distal end to the proximal end of the inner element 617, from a deepest end to a shallowest end.

Advantageously, as in the first 614 and second 615 embodiments of the inner element, an axial length of each of the inner hinges 680, 681, 682 is substantially equal to a multiple of the axial length D.

For example, the axial lengths of a first 680 and of a second 681 inner hinges are respectively equal to 3D and 2D. The axial length of a third inner hinge 682 is substantially equal to D, said third inner hinge being substantially identical to the inner hinges 80 described above.

In the first embodiment, the inner element 614 comprises three identical inner hinges 680. In the second embodiment, the inner element 615 comprises a first 680, a second 681 and a third 682 inner hinges different from each other.

Alternatively, in the third embodiment 616 of the inner element, an axial length of the inner hinge 683 is superior to the distance 664 between a pair of contiguous outer hinges 30 of the outer shaft 612, so that, according to a configuration of the surgical device, both of said contiguous outer hinges 30 face the inner hinge 683 at the same time.

Each pair of contiguous inner hinges 680, 681, 682, 683, 684, 685 is axially separated by a section 687 of the inner element 614, 615, 616, 617. The section 687 forms a continuous cylindrical surface and extends on a distance 688, 689, 690.

In the embodiments of FIG. 10, the distance 688, 689, 690 between a pair of contiguous inner hinges 680, 681, 682 is a multiple of the axial length D. Alternatively (not shown), the distance between a pair of contiguous inner hinges is superior to the distance 664 between a pair of contiguous outer hinges 30 of the outer shaft 612, so that, according to a configuration of the surgical device, both of said contiguous outer hinges 30 face the section 687 at the same time.

In the first embodiment 614 of the inner element, each pair of contiguous inner hinges 680 is separated by a same distance 688. In the embodiment shown on FIG. 10, said distance is equal to 2D. In an alternative embodiment, said distance is equal to 4D.

In the second embodiment 615 of the inner element, each pair of contiguous inner hinges 680, 681, 682 is separated by a difference distance 689, 690. A first distance 689 between the first 680 and the second 681 inner hinges is equal to 3D and a second distance 690 between the second 681 and the third 682 inner hinges is equal to 4D. Other values are possible, such as 4D for the first distance and 5D for the second distance.

In the embodiments of FIG. 10, the distal end of the inner element 614, 615, 616, 617 includes a flat edge 678. An end section 691 is comprised between said flat edge and the closest inner hinge 680. The end section 691 forms a continuous cylindrical surface having an axial length 692.

In the present embodiment, the axial length 692 is a multiple of the axial length D. More precisely, in the embodiments of FIG. 10, the axial length 692 is equal to 3D. In an alternative embodiment (not shown), the axial length 692 is equal to D.

The inner element 614, 615, 616, 617 is able to be inserted in the tubular outer shaft 612 in an assembled configuration, as described above for other embodiments of the invention. In the assembled configuration, the first 20 and second 70 main axes are merged.

Similarly to the other embodiments described above, a local stiffness of the surgical device 610 thus formed, considered at a specific outer hinge 30, can be modified in a controlled manner by axially moving and optionally rotating the inner element 614, 615, 616 or 617 in the tubular outer shaft 612.

As described above, an activated state "1" and a blocked state "0", respectively corresponding to a lower and to a higher stiffness, are considered. The blocked state "0" of an outer hinge 30 corresponds to said outer hinge axially facing a section 687 or the end section 691 of the inner element 614, 615.

The activated state "1" of an outer hinge 30 correspond to said outer hinge axially facing an inner hinge 680, 681, 682, 683, 684, 685. However, due to the elongated shape of some of the inner hinges 680, 681, 683, the activated state "1" may correspond to the outer hinge 30 axially facing a proximal end or a distal end of said inner hinge 680, 681, or being situated at equal distances to said proximal and distal ends. For the inner hinges 684, 685 having variable depths, the activated state "1" corresponds to a variety of axial positions of the outer hinge 30 between the deepest and shallowest ends of the corresponding inner hinge. The resulting stiffness may therefore vary progressively.

With inner elements 614, 615, 616, 617 corresponding to the embodiments of FIG. 10, it is possible to modify the stiffness configuration of the surgical device 610 by translating the inner elements in the tubular outer shaft 612. The stiffness transition occurs without stiff transition, that is, at least one of the outer hinges remains in the activated state "1" during the translation between two different configurations of the surgical device.

More preferably, two partially activated configurations succeed one to another without passing into the totally blocked configuration "0.0.0" described above.

By "partially activated configuration", it is meant a configuration with at least an outer hinge in the activated state "1".

For example, the tubular outer shaft 612 and the first embodiment 614 of the inner element are considered in the assembled configuration, with the distal end of said inner element 614 being the closest to the distal end 626 of said tubular outer shaft. The surgical device is in the totally blocked configuration "0.0.0" described above.

By axially moving the inner element 614 toward the proximal end of the tubular outer shaft 612, the partially activated configurations "1.0.0", "1.1.0", "1.1.1", "0.1.1", "0.0.1", "0.0.0" described above are successively obtained, without attaining the totally blocked configuration "0.0.0" between two partially activated configurations.

A similar result is obtained by replacing the first embodiment 614 by the second embodiment 615 of the inner element. However, the above-mentioned order of the partially activated configurations is obtained by moving the inner element 615 toward the distal end of the tubular outer shaft 612.

More precisely, the second embodiment 615 of the inner element is able to move axially in the tubular outer shaft 612. In a first configuration "1.1.1", each of the inner hinges 680, 681, 682 is axially level to one of the outer hinges 30.

A second configuration corresponds to an axial displacement of the inner element 615 in the tubular outer shaft toward the distal end 626, on a distance corresponding to the axial length D. In the second configuration "1.1.0", the inner hinge 682 is axially distant from the corresponding outer hinge and each of the inner hinges 680 and 681 are axially facing the corresponding outer hinge.

The other configurations mentioned above are obtained in a similar manner.

The embodiments of FIG. 10 allows to choose the translation direction between the tubular outer shaft and inner element for a particular succession of partially activated configurations.

The illustrative examples of surgical devices 10, 110, 210, 310, 410, 610 presented above comprise a limited number of outer hinges and inner hinges. With similar embodiments comprising a higher number of outer and inner hinges, it is possible to precisely control the stiffness of the surgical device along a significant length close to the distal end. It is thus possible to assist a displacement of the device along a complex 3D-path in a patient's body.

Preferably, said control is carried out by a combined motion of translation and rotation of the inner element in the tubular outer shaft.

In an embodiment, the surgical device comprises a control handle connected to the proximal end of the surgical device. An example of control handle 700 is shown on FIG. 1, connected to the proximal end of a surgical device 710, similar to the surgical devices 10, 110, 210, 310, 410, 610 presented above.

The control handle 700 comprises: a hollow body 701, extending along an axis 702 designed as moving axis; and a strip 703 received in the hollow body 701. The strip 703 is movable relative to the body 701 according to the moving axis 702.

The body 701 comprises a longitudinal slot 704; and a plurality of grooves 705 formed in an inner surface of said body. The grooves 705 extend perpendicularly to the moving axis 702.

The strip 703 comprises: a lateral extension 706, able to slide in the longitudinal slot 704 of the body; and an elastic member 707. The elastic member 707 is able to elastically clip into each of the grooves 705 of the body.

An end of the lateral extension 706 forms an activation button 708. By acting on the activation button 708, an operator is able to axially move the strip 703 relative to the body. Said movement allows the elastic member 707 to successively clip into adjacent grooves 705.

The elastic member 707 being clipped in a particular groove 705 corresponds to a particular axial position of the strip 703, and of the activation button 708, relative to the body 701. Preferably, an outer surface of the body 701 includes visual signs along the longitudinal slot 704, allowing to associate an axial position of the activation button 708 to the coupling of the elastic member 707 to a particular groove 705.

In the configuration shown on FIG. 1, the proximal ends 22 and 72 of the outer shaft 12 and inner element 14 of the surgical device 710 are connected, respectively, to the body 701 and to the strip 703. By pushing the activation button 708 along the moving axis 702, the operator is able to axially move the inner element 14 relative to the outer shaft 12. Preferably, the grooves 705 and elastic member 707 are configured so that a coupling of the elastic member 707 to a particular groove 705 correspond to an axial position of the inner element allowing to obtain a particular stiffness on each of the outer hinges 30 of the outer shaft 12.

The handle 700 is designed for a purely axial movement of the inner element 14 relative to the outer shaft 12. In another embodiment (not shown), the handle is designed for a combined axial and angular movement of the inner element 14 relative to the outer shaft 12.

In the embodiment of FIG. 5, the locking mechanism allows to lock/unlock an axial position of the inner element 414 relative to the tubular outer shaft 412.

More precisely, as the crown 493 of the inner element 414 is axially facing the or one of the groove(s) 468 of the tubular outer shaft 412, a first angular configuration of the inner element 414 allows said crown 493 and groove 468 to fit in, so as to axially block the course of the inner element in the tubular outer shaft 412. For example, the crown 493 and groove 468 have complementary elliptical shapes and the first angular configuration corresponds to the major axes being perpendicular.

Moreover, a second angular configuration of the inner element 414 allows the crown 493 to disengage from the groove 468, so as to release the inner element for translation in the tubular outer shaft 412. For example, the second angular configuration corresponds to the major axes of the ellipses being perpendicular.

When activated, the locking mechanism allows a transfer of compressive axial load from the tubular outer shaft 412 to the inner element 414. Such a load transfer may prevent an unwanted buckling of the outer hinges 430 during the insertion of the surgical device 410 in biological tissues.

Such a locking mechanism may be used in other embodiments of the invention, wherein the inner element is able to translate in the tubular outer shaft.

In another embodiment (not shown) similar to the embodiment of FIG. 5, the locking mechanism allowing to lock/unlock an axial position of the inner element 414 relative to the tubular outer shaft 412 comprises a first threaded part located on the tubular outer shaft 412 and a second threaded part located on the inner element 414, the first and second threaded parts being complementary to each other and able to be reversibly assembled to one another.

The tubular outer shaft, the inner element and the optional core element of the surgical devices of the invention are manufactured in materials suitable for surgical use. According to an embodiment, the tubular outer shaft and/or the inner element and/or the core element are manufactured in a metallic material, such as nitinol or titanium. According to another embodiment, the tubular outer shaft and/or the inner element and/or the core element are manufactured in a polymeric material, such as polyoxymethylene (POM) or polyether ether ketone (PEEK).

According to another embodiment, the tubular outer shaft and/or the inner element and/or the core element are manufactured in glass, more specifically in fused silica. Such a manufacturing is for example similar to the micro-scale manufacturing of a glass surgical tool, also known as 3D-femto laser printing, described by M. Zanaty et. al., *Proceeding of the Design of Medical Devices Conference*, p. 1, ASME, Eindhoven, Netherlands, 2017.

The 3D-femto laser printing of fused silica allows complex 3D devices to be achieved in two steps, which are laser exposure followed by material removal with HF or a similar acid. Monobloc devices can be obtained, requiring no or little assembly. The process is adapted to devices of very small size. The obtained devices can be sterilized and are bio-compatible.

According to embodiments of the invention, such as the embodiments of FIG. 1 or FIGS. 3-4, the surgical device 10, 210, 310 is a biopsy needle, similar to the needle of previously cited document U.S. Pat. No. 8,057,403.

According to other embodiments of the invention, the surgical device is an injection needle, a drug delivery needle, an anesthesia needle, a chemical marker needle, a guide, a channel or an optical tool/endoscope. Alternatively, the surgical device comprises an interventional mechanical tool or a tool for electrotherapy, cryotherapy, ciment injection or liquid removal.

According to other embodiments of the invention, the surgical device is designed for percutaneous ablation, by methods including ethanol injection, microwave ablation (MWA), radiofrequency ablation (RFA), irreversible electroporation (IRE), and cryoablation.

According to other embodiments of the invention, the surgical device is designed for high-dose-rate therapies and cell-based therapies.

According to other embodiments of the invention, the surgical device is a MIS (minimally invasive surgery) flexible-on-demand tool.

A surgical method involving a surgical device according to the invention will now be described. Under optional medical imaging monitoring, such as MRI-monitoring, the distal end of the surgical device is inserted into biological tissues, such as the body of a patient. Said distal end is oriented toward a target, such as an organ of the body, for example the liver. The surgical device is then progressively pushed in the corresponding direction by a surgeon.

The path of the distal end in the body is followed by the surgeon through an imaging device such as MRI or scanner. Depending on the tissues and/or organs occurring on said path, the stiffness of the distal end is progressively adapted by the surgeon in order to allow said distal end to bend, or inversely to pursue a straight path. As described above, the stiffness of the distal end is locally adapted by translating and/or rotating the inner element relative to the tubular outer shaft of the surgical device. As described above, the adaptation of the stiffness may be carried out by means of a control handle of the surgical device, such as the handle 700.

In embodiments wherein the first and second outer slits of the distal and proximal outer hinges face each other relative to distinct longitudinal planes crossing the outer shaft, said longitudinal planes having different angular orientations, it is possible to bend the surgical device in more than one plane.

The surgical device of the invention allows a fine and accurate control of its stiffness in order to adapt to the environment of the path in the biological tissues. Therefore, the trajectory of the surgical device is precisely controlled, in order to reach the target without damaging other organs.

The invention claimed is:

1. A surgical device comprising a tubular outer shaft and an inner element, each of said outer shaft and said inner element having an elongated shape extending along a longitudinal axis between a proximal end and a distal end, the tubular outer shaft comprising at least a distal and a proximal outer hinges, the distal outer hinge being closer to the distal end than the proximal outer hinge; each outer hinge comprising a first and a second outer slits facing each other relative to a first longitudinal plane crossing the outer shaft and parallel to the longitudinal axis of said outer shaft, the inner element comprising at least one inner hinge, the at least one inner hinge comprising a first inner slit and a second inner slit facing each other relative to a second longitudinal plane crossing the inner element and parallel to the longitudinal axis of said inner element, the surgical device having: a first and a second distal stiffnesses considered at the distal outer hinge; and a first and a second proximal stiffnesses considered at the proximal outer hinge; each of the second distal and proximal stiffnesses being superior to, respectively, the first distal and proximal stiffness; and the inner element being able to move angularly and/or axially in the tubular outer shaft, between different configurations of the tubular outer shaft and the inner element relative to each other, wherein the first and the second distal stiffnesses correspond respectively to a first and to a second positions of the at least one inner hinge relative to the distal outer hinge, and that the first and the second proximal stiffnesses correspond respectively to a first and to a second positions of the at least one inner hinge relative to the proximal outer hinge; and wherein the surgical device is configured so that, in at least one of the configurations of the tubular outer shaft and the inner element, the surgical device has the second distal stiffness and the first proximal stiffness.

2. The surgical device according to claim 1, wherein:

the at least one inner hinge of the inner element is a distal inner hinge; and the inner element also comprises at least a proximal inner hinge, the distal inner hinge being closer to the distal end than the proximal inner hinge.

3. The surgical device according to claim 2, wherein:

the first and second outer slits of the distal and proximal outer hinges face each other relative to a same longitudinal plane crossing the outer shaft; and the first and second inner slits of the distal and proximal inner hinges face each other relative to distinct longitudinal planes crossing the inner element;

or the first and second outer slits of the distal and proximal outer hinges face each other relative to distinct longitudinal planes crossing the outer shaft; and the first and second inner slits of the distal and proximal inner hinges face each other relative to a same longitudinal plane crossing the inner element;

or the first and second outer slits of the distal and proximal outer hinges face each other relative to distinct longitudinal planes crossing the outer shaft; and the first and second inner slits of the distal and proximal inner hinges also face each other relative to distinct longitudinal planes crossing the inner element.

4. The surgical device according to claim 2, wherein: the distal and proximal outer hinges are contiguous; the distal and proximal inner hinges are contiguous; and a distance between the distal and proximal outer hinges is different from a distance between the distal and proximal inner hinges.

5. The surgical device according to claim 4, wherein the distance between the distal and proximal outer hinges is equal to a multiple of the distance between the distal and proximal inner hinges.

6. The surgical device according to claim 2, wherein the inner element also comprises a further inner hinge, the proximal inner hinge being closer to the distal end than the further inner hinge; the distal and proximal inner hinges are contiguous; the proximal and further inner hinges are contiguous; and a distance between the distal and proximal inner hinges is different from a distance between the proximal and further inner hinges.

7. The surgical device according to claim 1, wherein the outer shaft also comprises a further outer hinge, the proximal outer hinge being closer to the distal end than the further outer hinge, the surgical device having a first and a second further stiffnesses considered at the further outer hinge; the second further stiffness being superior to the first further stiffness.

8. The surgical device according to claim 7, configured so that, in the configuration with the second distal stiffness and the first proximal stiffness, the surgical device has the second further stiffness.

9. The surgical device according to claim 1, wherein each of the first and second outer slits of at least one outer hinge comprise: a notch extending between two ends; and two curved cuts, each curved cut being connected to one end of the notch.

10. The surgical device according to claim 1, wherein the distal end of the outer shaft and/or of the inner element includes a pointed tip.

11. The surgical device according to claim 1, wherein:

the inner element is tubular; and the surgical device also comprises a core element having an elongated shape extending between a proximal end and a distal end, said core element being able to move angularly and/or axially in the inner element.

12. The surgical device according to claim 11, wherein the distal end of the core element includes a pointed tip.

13. The surgical device according to claim 1, wherein the at least one inner hinge has an axial length superior to an axial length (D) of the outer hinges.

14. The surgical device according to claim 13, wherein the axial length of the at least one inner hinge is equal to a multiple of the axial length (D) of the outer hinges.

15. The surgical device according to claim 13, wherein the inner element comprises at least a pair of contiguous inner hinges and wherein a distance between said pair of contiguous inner hinges is a multiple of the axial length (D) of the outer hinges.

16. The surgical device according to claim 13, wherein the inner element comprises at least a first and a second inner hinges, at least said first inner hinge having an axial length superior to the axial length (D) of the outer hinges;

wherein the inner element is able to move axially in the tubular outer shaft, between a first and a second configurations, a first of the proximal and distal outer hinges being axially level with the first inner hinge in both of said first and second configurations, so that, considered at said first outer hinge, the surgical device has the first stiffness in both of said first and second configurations; and the second of the proximal and distal outer hinges is axially level with the second inner hinge in the first configuration and axially distant from the second inner hinge in the second configuration, so that, considered at said second outer hinge, the surgical device has the first stiffness in the first configuration and the second stiffness in the second configuration.

17. The surgical device according to claim 1, wherein the inner element is able to move axially in the tubular outer shaft, between different configurations of the tubular outer shaft and the inner element relative to each other.

18. The surgical device according to claim 17, wherein the inner element is able to move axially and angularly in the tubular outer shaft, between different configurations of the tubular outer shaft and the inner element relative to each other.

19. The surgical device according to claim 1, also comprising a locking mechanism allowing to lock/unlock an axial position of the inner element relative to the tubular outer shaft.

* * * * *